United States Patent
Lasko et al.

(10) Patent No.: US 8,788,049 B2
(45) Date of Patent: Jul. 22, 2014

(54) FUNCTIONAL ELECTRICAL STIMULATION SYSTEMS

(75) Inventors: Eyal Lasko, Tel Mond (IL); Shmuel Springer, Modi'in (IL); Mark Rubin, Moshav Nitzanai Oz (IL); Amit Dar, Kfar Hes (IL)

(73) Assignee: Bioness Neuromodulation Ltd., Raanana (IL)

( * ) Notice: Subject to any disclaimer, the term of this patent is extended or adjusted under 35 U.S.C. 154(b) by 1301 days.

(21) Appl. No.: 12/299,043

(22) PCT Filed: May 1, 2007

(86) PCT No.: PCT/IL2007/000531
§ 371 (c)(1),
(2), (4) Date: Oct. 30, 2008

(87) PCT Pub. No.: WO2007/125534
PCT Pub. Date: Nov. 8, 2007

(65) Prior Publication Data
US 2009/0069865 A1    Mar. 12, 2009

Related U.S. Application Data

(60) Provisional application No. 60/746,060, filed on May 1, 2006, provisional application No. 60/805,359, filed on Jun. 21, 2006.

(30) Foreign Application Priority Data

Nov. 16, 2006   (WO) .................. PCT/IL2006/001326

(51) Int. Cl.
*A61N 1/00*    (2006.01)
(52) U.S. Cl.
USPC ......................................................... 607/48
(58) Field of Classification Search
USPC .................................................. 607/48–49
See application file for complete search history.

(56) References Cited

U.S. PATENT DOCUMENTS

| 3,204,637 | A | 9/1965 | Frank et al. |
| 3,344,792 | A | 10/1967 | Offner et al. |

(Continued)

FOREIGN PATENT DOCUMENTS

| DE | 19830359 A1 | 1/2000 |
| EP | 1508302 | 2/2005 |

(Continued)

OTHER PUBLICATIONS

Final Office Action for U.S. Appl. No. 10/335,905, mailed Jun. 11, 2009.

(Continued)

*Primary Examiner* — Christopher D Koharski
*Assistant Examiner* — Roland Dinga

(57) ABSTRACT

A gait modulation system including: (a) a sensor device including a sensor adapted for associating with at least one lower limb of the patient, the sensor for transducing at least one parameter related to a gait of the patient, so as to obtain gait data related to the gait, and (b) a muscle stimulator including: (i) an electrical stimulation circuit, the circuit adapted to supply an electrical stimulation output to an electrode array for performing functional electrical stimulation of at least one muscle of the lower limb, and (ii) a microprocessor, operatively connected to the at least one sensor, the microprocessor adapted for: receiving a stream of gait information based on the gait data; processing the gait information, and controlling the stimulation output based on the processing of the gait information, and wherein the microprocessor is further adapted to identify a failure in the stream of gait information, and to consequently control the electrical stimulation circuit to deliver a fail-safe stimulation output over a portion of a duration of the failure.

19 Claims, 11 Drawing Sheets

(56) References Cited

U.S. PATENT DOCUMENTS

| | | | |
|---|---|---|---|
| 3,426,748 A | 2/1969 | Bowers | |
| 3,881,496 A * | 5/1975 | Vredenbregt et al. | 607/49 |
| 3,941,137 A * | 3/1976 | Vredenbregt et al. | 607/49 |
| 4,381,012 A | 4/1983 | Russek | |
| 4,432,368 A | 2/1984 | Russek | |
| 4,528,984 A | 7/1985 | Morawetz et al. | |
| 4,558,704 A | 12/1985 | Petrofsky | |
| 4,569,352 A * | 2/1986 | Petrofsky et al. | 607/49 |
| 4,580,569 A | 4/1986 | Petrofsky | |
| 4,586,495 A | 5/1986 | Petrofsky | |
| 4,647,918 A | 3/1987 | Goforth | |
| 4,697,808 A | 10/1987 | Larson et al. | |
| 4,745,930 A | 5/1988 | Confer | |
| 4,832,033 A | 5/1989 | Maher et al. | |
| 4,976,264 A | 12/1990 | Petrofsky | |
| 4,996,987 A | 3/1991 | Petrofsky | |
| 5,016,635 A | 5/1991 | Graupe | |
| 5,081,989 A | 1/1992 | Graupe et al. | |
| 5,112,296 A * | 5/1992 | Beard et al. | 602/28 |
| 5,121,747 A | 6/1992 | Andrews | |
| 5,167,229 A | 12/1992 | Peckham et al. | |
| 5,285,781 A | 2/1994 | Brodard | |
| 5,330,516 A | 7/1994 | Nathan | |
| 5,350,414 A | 9/1994 | Kolen | |
| 5,357,696 A | 10/1994 | Gray et al. | |
| 5,408,873 A | 4/1995 | Schmidt et al. | |
| 5,433,737 A | 7/1995 | Aimone | |
| 5,476,441 A * | 12/1995 | Durfee et al. | 602/23 |
| 5,487,759 A | 1/1996 | Bastyr et al. | |
| 5,540,735 A | 7/1996 | Wingrove | |
| 5,562,707 A | 10/1996 | Prochazka et al. | |
| 5,566,479 A | 10/1996 | Gray et al. | |
| 5,628,722 A | 5/1997 | Solomonow et al. | |
| 5,643,332 A | 7/1997 | Stein | |
| 5,664,346 A | 9/1997 | Barker | |
| 5,724,996 A | 3/1998 | Piunti | |
| 5,748,845 A | 5/1998 | Labun et al. | |
| 5,775,332 A | 7/1998 | Goldman | |
| 5,814,093 A | 9/1998 | Stein | |
| 5,843,142 A * | 12/1998 | Sultan | 607/49 |
| 5,851,191 A | 12/1998 | Gozani | |
| 5,861,017 A | 1/1999 | Smith et al. | |
| 5,916,159 A | 6/1999 | Kelly et al. | |
| 5,951,598 A | 9/1999 | Bishay et al. | |
| 5,980,472 A | 11/1999 | Seyl | |
| 5,983,140 A * | 11/1999 | Smith et al. | 607/59 |
| 6,002,965 A | 12/1999 | Katz et al. | |
| 6,064,912 A | 5/2000 | Kenney | |
| 6,126,355 A | 10/2000 | Clover, Jr. | |
| 6,132,386 A | 10/2000 | Gozani | |
| 6,174,294 B1 | 1/2001 | Crabb et al. | |
| 6,195,921 B1 | 3/2001 | Truong | |
| 6,246,863 B1 | 6/2001 | Kampel | |
| 6,282,448 B1 | 8/2001 | Katz et al. | |
| 6,308,102 B1 | 10/2001 | Sieracki et al. | |
| 6,349,126 B2 | 2/2002 | Ogawa et al. | |
| 6,438,428 B1 | 8/2002 | Axelgaard et al. | |
| 6,456,885 B1 | 9/2002 | Shiba et al. | |
| 6,496,739 B2 | 12/2002 | Arbel | |
| 6,507,757 B1 * | 1/2003 | Swain et al. | 607/49 |
| 6,516,500 B2 | 2/2003 | Ogino et al. | |
| 6,564,103 B2 | 5/2003 | Fischer et al. | |
| 6,571,115 B2 | 5/2003 | Axelgaard et al. | |
| 6,587,728 B2 | 7/2003 | Fang et al. | |
| 6,651,352 B2 | 11/2003 | McGorry et al. | |
| 6,700,499 B2 | 3/2004 | Kubo et al. | |
| D494,273 S | 8/2004 | Haugland et al. | |
| 6,829,510 B2 | 12/2004 | Nathan et al. | |
| 6,836,744 B1 | 12/2004 | Asphahani et al. | |
| 6,978,684 B2 * | 12/2005 | Nurse | 73/862.041 |
| 6,988,005 B2 | 1/2006 | McGraw et al. | |
| 7,162,305 B2 * | 1/2007 | Tong et al. | 607/48 |
| 7,200,517 B2 | 4/2007 | Darley et al. | |
| 7,257,448 B2 | 8/2007 | Crowe et al. | |
| 7,337,007 B2 | 2/2008 | Nathan et al. | |
| 7,359,751 B1 | 4/2008 | Erickson et al. | |
| 7,403,821 B2 | 7/2008 | Haugland et al. | |
| 7,410,471 B1 | 8/2008 | Campbell et al. | |
| 7,537,573 B2 | 5/2009 | Horst | |
| 7,632,239 B2 | 12/2009 | Dar et al. | |
| 7,713,217 B2 | 5/2010 | Ikeuchi et al. | |
| 7,756,585 B2 | 7/2010 | Embrey et al. | |
| 7,785,279 B2 | 8/2010 | Sankai | |
| 8,070,703 B2 | 12/2011 | Skahan et al. | |
| 8,382,688 B2 | 2/2013 | Dar et al. | |
| 2001/0039444 A1 | 11/2001 | Bar-Or et al. | |
| 2002/0077688 A1 | 6/2002 | Kirkland | |
| 2003/0083596 A1 | 5/2003 | Kramer et al. | |
| 2003/0114892 A1 | 6/2003 | Nathan et al. | |
| 2003/0114894 A1 * | 6/2003 | Dar et al. | 607/48 |
| 2004/0011366 A1 | 1/2004 | Schulman et al. | |
| 2004/0044381 A1 | 3/2004 | Duncan et al. | |
| 2004/0082979 A1 * | 4/2004 | Tong et al. | 607/48 |
| 2004/0122483 A1 * | 6/2004 | Nathan et al. | 607/49 |
| 2004/0133081 A1 | 7/2004 | Teller et al. | |
| 2004/0147975 A1 * | 7/2004 | Popovic et al. | 607/48 |
| 2004/0172097 A1 * | 9/2004 | Brodard et al. | 607/49 |
| 2004/0173220 A1 * | 9/2004 | Harry et al. | 128/892 |
| 2004/0243197 A1 | 12/2004 | Demian | |
| 2004/0249316 A1 * | 12/2004 | Ashihara et al. | 600/595 |
| 2005/0043660 A1 | 2/2005 | Stark et al. | |
| 2005/0049652 A1 * | 3/2005 | Tong | 607/48 |
| 2005/0131317 A1 * | 6/2005 | Oddsson et al. | 600/592 |
| 2005/0192645 A1 | 9/2005 | Stein et al. | |
| 2005/0261609 A1 | 11/2005 | Collings et al. | |
| 2006/0015470 A1 | 1/2006 | Lauer et al. | |
| 2006/0020421 A1 | 1/2006 | Darley et al. | |
| 2006/0211956 A1 | 9/2006 | Sankai | |
| 2006/0276704 A1 | 12/2006 | McGinnis et al. | |
| 2006/0282017 A1 | 12/2006 | Avni et al. | |
| 2006/0282018 A1 | 12/2006 | Balzano | |
| 2007/0021689 A1 | 1/2007 | Stergiou et al. | |
| 2007/0112394 A1 * | 5/2007 | Nathan et al. | 607/49 |
| 2007/0123756 A1 | 5/2007 | Kitajima et al. | |
| 2007/0179560 A1 | 8/2007 | Tong et al. | |
| 2007/0203533 A1 * | 8/2007 | Goren et al. | 607/49 |
| 2008/0033505 A1 | 2/2008 | Davis et al. | |
| 2008/0140154 A1 | 6/2008 | Loeb et al. | |
| 2008/0177355 A1 | 7/2008 | Miesel et al. | |
| 2008/0319349 A1 | 12/2008 | Zilberman | |
| 2009/0012436 A1 | 1/2009 | Lanfermann et al. | |
| 2009/0043357 A1 | 2/2009 | Tong et al. | |
| 2009/0177131 A1 * | 7/2009 | Dar et al. | 602/2 |
| 2011/0137375 A1 | 6/2011 | McBride | |
| 2012/0203156 A1 | 8/2012 | Dar et al. | |
| 2012/0330375 A1 | 12/2012 | Nathan et al. | |
| 2012/0330394 A1 | 12/2012 | Dar et al. | |
| 2012/0330395 A1 | 12/2012 | Dar et al. | |

FOREIGN PATENT DOCUMENTS

| | | |
|---|---|---|
| JP | 1985-119949 A | 6/1985 |
| JP | 1994-501854 T | 3/1994 |
| JP | 2002-191580 A | 7/2002 |
| JP | 2004-503266 T | 2/2004 |
| JP | 2004-215735 A | 8/2004 |
| JP | 2004-313555 A | 11/2004 |
| JP | 2005-514143 T | 5/2005 |
| JP | 2006-166244 A | 6/2006 |
| JP | 2006-192276 | 7/2006 |
| WO | WO 2008/005865 | 1/2008 |

OTHER PUBLICATIONS

Final Office Action for U.S. Appl. No. 10/335,905, mailed Apr. 18, 2008.

Non-Final Office Action for U.S. Appl. No. 10/335,905, mailed Dec. 19, 2005.

Office Action for U.S. Appl. No. 10/335,905, mailed Apr. 2, 2010.

Supplementary European Search Report for European Application No. 07736271.3, mailed Mar. 18, 2010.

Office Action for U.S. Appl. No. 10/335,905, mailed Jan. 30, 2007.

Office Action for U.S. Appl. No. 10/335,905, mailed Dec. 24, 2008.

(56) References Cited

OTHER PUBLICATIONS

Strojnik, P., Acimovic, R., Vavken, E., Simic, V. and Stanic, U. "Treatment of drop foot using an implantable peroneal underknee stimulator." Scandanavian J. of Rehabil. Med. 19:37-43, 1987.
Kralj, A.R. & Bajd, T., "Functional Electrical Stimulation: Standing and Walking after Spinal Cord Injury," CRC Press, Boca Raton, FL., pp. 1-15, 1989.
Lieberson et al., "Functional Electrotherapy: Stimulation of the Peroneal Nerve Synchronized with the Swing Phase of the Gait of Hemiplegic Patients," 3rd Int. Congress of Physical Medicine, Session on Neuromuscular Diseases, Washington DC, Aug. 25, 1960.
Popovic, et al., "Functional Electrical Stimulation for Grasping and Walking: Indications and Limitations," Spinal Cord, Jun. 2001.
Popovic, et al., "Surface Stimulation Technology for Grasping and Walking Neuroprostheses—Improving Quality of Life in Stroke/Spinal Cord Injury Subjects with Rapid Prototyping and Portable FES Systems," IEEE Engineering in Medicine and Biology, Jan./Feb. 2001.
International Preliminary Report on Patentability for PCT/IL07/00531, mailed on Mar. 19, 2009; 5 pages.
International Search Report for PCT/IL07/00531, mailed on Jul. 7, 2008; 2 pages.
Office Action for Australian Patent Application No. AU 2006236428, mailed Jan. 25, 2010.
Office Action for European Patent Application No. EP 06750483.7, mailed Apr. 16, 2009, 5 pages.
International Search Report and Written Opinion for PCT/US06/014455, mailed Aug. 8, 2006.
Office Action for U.S. Appl. No. 12/630,199, mailed Jun. 21, 2011.
International Search Report and Written Opinion for International Application No. PCT/US2010/058483, mailed Feb. 7, 2011.
Office Action for Canadian Application No. 2,632,196, mailed on Mar. 16, 2010.
Office Action for U.S. Appl. No. 11/552,997 mailed Mar. 24, 2009.
Office Action for U.S. Appl. No. 11/552,997 mailed Oct. 30, 2007.
Office Action for U.S. Appl. No. 11/552,997 mailed Aug. 5, 2008.
Examination Report for European Application No. 07736271.3, mailed on Dec. 14, 2010.
Examination Report for European Application No. 07736271.3, mailed on Nov. 14, 2011.
Notice of Reasons for Rejection for Japanese Patent Application No. 2009-517597, mailed Jan. 23, 2012.
Office Action for U.S. Appl. No. 12/631,095, mailed Sep. 14, 2011.
Office Action for U.S. Appl. No. 10/335,905, mailed Jan. 14, 2011.
Ness H200 Product Specifications "H200™ Overview& Product Specifications," [online] 2006 [retrieved on Jun. 5, 2007]. Retrieved from the Internet: URL: <http://www.bionessinc.com/products/h200/htm>.
Wood, D.E., "Spatial sensitivity comparisons between an implanted and surface dropped foot neuromuscular stimulator," 9th Annual Conference of the International FES Society, Sep. 2004.
Stralka, "Gait Training (by Stimulating Dorsiflexors)," NM III™ Neuromuscular Stimulation System Suggested Protocol, NM III Program Set #2 Program F, Rehabilicare® 920080 Rev. C.
Neurodan "ActiGait® An implantable drop foot correction system," Neurodan A/S—Products—ActiGait® [online] [retrieved on Jun. 5, 2007]. Retrieved from the Internet: URL: <http://www.neurodan.com/actigait.asp>.
NDI Medical "About Odfs Dropped Foot Stimulator," [online] 2005 [retrieved on Jun. 5, 2006]. Retrieved from the Internet: URL: <http://www.odfs.com/About_ODFS/about_odfs.html>.
NMES Guidelines for Treatment "Gait Training," [online] [retrieved on May 30, 2007]. Retrieved from the Internet: URL: <http://www.empi.com/products1nmes/gait.pdf>.
Waters, R.L. et al., "Experimental correction of footdrop by electrical stimulation of the peroneal nerve," J Bone Joint Surg Am., vol. 38, No. 8 (Dec. 1975), pp. 1047-1054.
Sowerbutt, C., "Restoring Gait in Stroke Patients Using Functional Neuromuscular Stimulation," [online] Sep. 1, 2006 [retrieved on May 30, 2007]. Retrieved from the Internet: URL: <http://appneurology.com/showArticle.jhtml?print=true&articleID=193104432>.
Office Action for U.S. Appl. No. 12/630,199, mailed Jan. 18, 2012.
Examiner's Answer to Appeal Brief for U.S. Appl. No. 12/630,199, mailed Aug. 14, 2012.
Office Action for Australian Patent Application No. AU 2007245258, dated Apr. 12, 2012.
Notice of Reasons for Rejection for Japanese Patent Application No. 2009-517597, mailed Nov. 2, 2012.
Office Action for Canadian Application No. 2,649,663, mailed Nov. 20, 2013, 3 pages.
European Search Report for European Application No. EP 12197261.6, mailed Mar. 28, 2013.
Alon, G. et al., "Persons with C5 or C6 tetraplegia achieve selected functional gains using a neuroprosthesis," Arch. Phys. Med. Rehabil., 84:119-124 (Jan. 2003).
"Clinical evaluation of the Ijubljana functional electrical peroneal brace," Subcommittee on Evaluation, Committee on Prosthetics Research and Development Division of Medical Sciences—National Research Council, National Academy of Sciences, Washington, D.C., Report E-7 (1973).
Daly, W. K., "Electrodes installed in roll-on suspension sleeves," From "MEC '02 The Next Generation," Proceedings of the 2002 MyoElectric Controls/Powered Prosthetics Symposium, Fredericton, New Brunswick, Canada: Aug. 21-23, 2002, University of New Brunswick, 3 pages.
Davis, R. et al., "Evaluation of electrical stimulation as a treatment for the reduction of spasticity," Bulletin of Prosthetics Research, Department of Medicine and Surgery Veterans Administration, Washington, D.C., pp. 302-309 (1974).
Duncan, R. M., "Basic principles of splinting the hand," Journal of the American Physical Therapy Association, 69(12):1104-1116 (1989).
Hart, R. L. et al., "A comparison between control methods for implanted FES hand-grasp systems," IEEE Transactions on Rehabilitation Engineering, 6(2):208-218 (Jun. 1998).
Hendricks, H. T. et al., "Functional electrical stimulation by means of the 'Ness Handmaster Orthosis' in chronic stroke patients: an exploratory study," Clinical Rehabilitation, 15:217-220 (2001).
Kralj, A. et al., "Functional electrical stimulation of the extremities: part 1," Journal of Medical Engineering and Technology, pp. 12-15 (Jan. 1977).
Kralj, A. et al., "Functional electrical stimulation of the extremities: part 2," Journal of Medical Engineering and Technology, pp. 75-80 (Mar. 1977).
Popovic, M. R. et al., "Neuroprostheses for grasping," Neurological Research, 24:443-452 (Jul. 2002).
Popovic, M. R. et al., "Functional electrical therapy: retraining grasping in spinal cord injury," Spinal Cord, 44:143-151 (2006).
Prochazka, A. et al., "The bionic glove: An electrical stimulator garment that provides controlled grasp and hand opening in quadriplegia," Arch. Phys. Med. Rehabil., 78:608-614 (Jun. 1997).
Stanic, U., "History of functional electrical stimulation," International Functional Electrical Stimulation Society, INS & IFESS Joint Congress, Sep. 16-20, 1998, Lucerne, Switzerland, 37 pages.
Stopar, M. et al., "New stimulators for cutaneous stimulation," Advances in External Control of Human Extremities, Proceedings of the Seventh International Symposium on External Control of Human Extremities, pp. 267-272 (1981).
Strojnik, P. et al., "Implantable stimulators for neuromuscular control," Chapter 78 in The Biomedical Engineering Handbook: Second Edition, Bronzino, J. D. (ed.), Boca Raton: CRC Press LLC (2000), 15 pages.
Uellendahl, J. E. et al., "Custom silicone sockets for myoelectric prostheses," Journal of Prosthetics and Orthotics, 18(2):35-40 (2006).
Uellendahl, J. E. et al., "Custom silicone sockets for myoelectric prostheses," From "MEC '05 Intergrating Prosthetics and Medicine," Proceedings of the 2005 MyoElectric Controls/Powered Prosthetics Symposium, held in Fredericton, New Brunswick, Canada, Aug. 17-19, 2005, 6 pages.

(56) References Cited

OTHER PUBLICATIONS

Vodovnik, L. et al., "Functional electrical stimulation for control of locomotor systems," CRC Critical Reviews in Bioengineering, 6(2):63-131 (Sep. 1981).

Ward, A. R. et al., "Russian electrical stimulation: The early experiments," Physical Therapy, 82(10):1019-1030 (Oct. 2002).

Waters, R. L. et al., "Effectiveness of selected surface electrodes for motor stimulation," Advances in External Control of Human Extremities, Proceedings of the Sixth International Symposium on External Control of Human Extremities, pp. 31-38 (1978).

Waters, R. et al., "Treatment of the hemiplegic upper extremity using electrical stimulation and biofeedback training," Report to the Veterans Administration, Contract V600P-1064-79, Funding Period Sep. 27, 1979-Sep. 30, 1980, pp. 251-266.

Supplementary European Search Report for European Application No. 10835019.0, mailed Feb. 12, 2014.

* cited by examiner

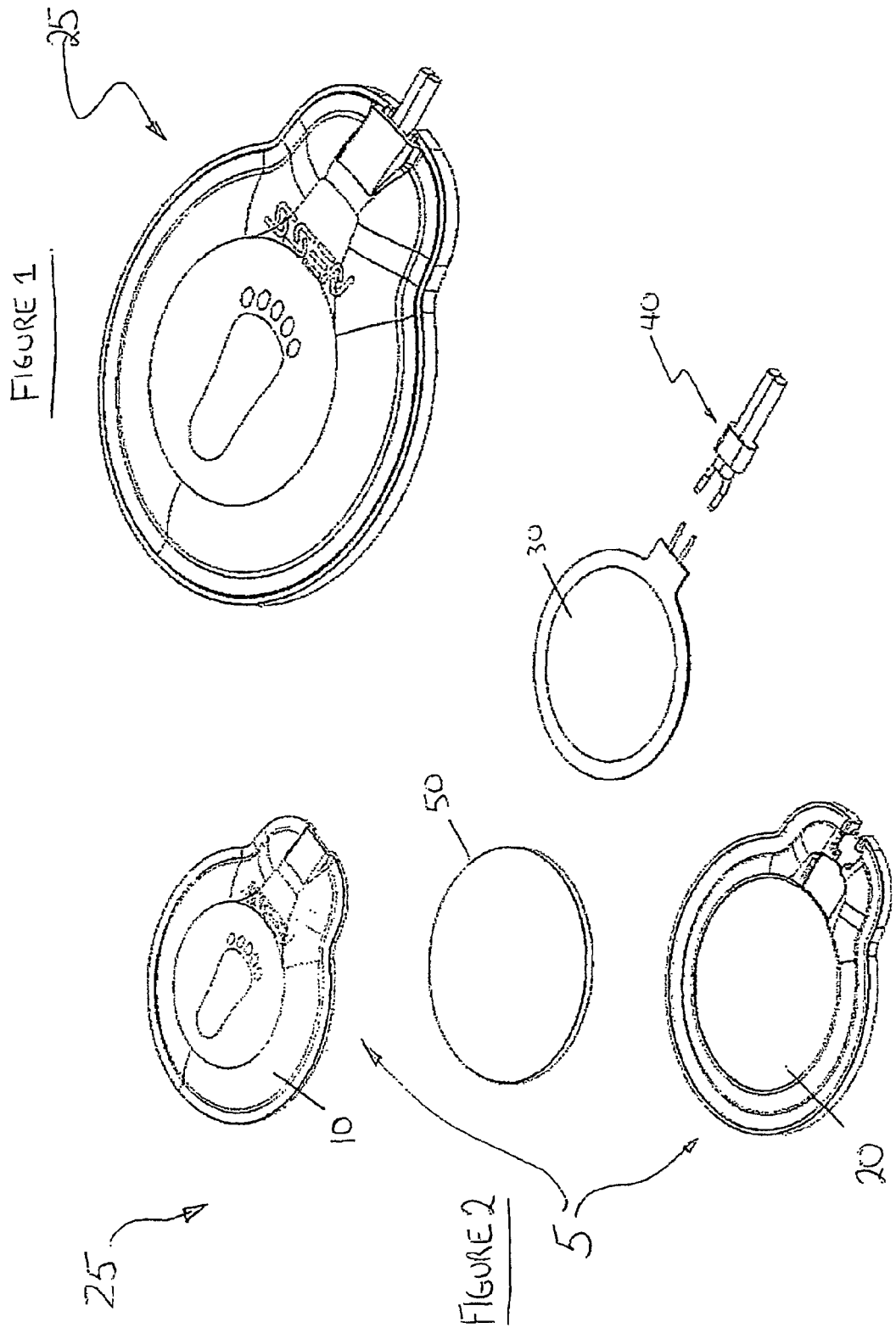

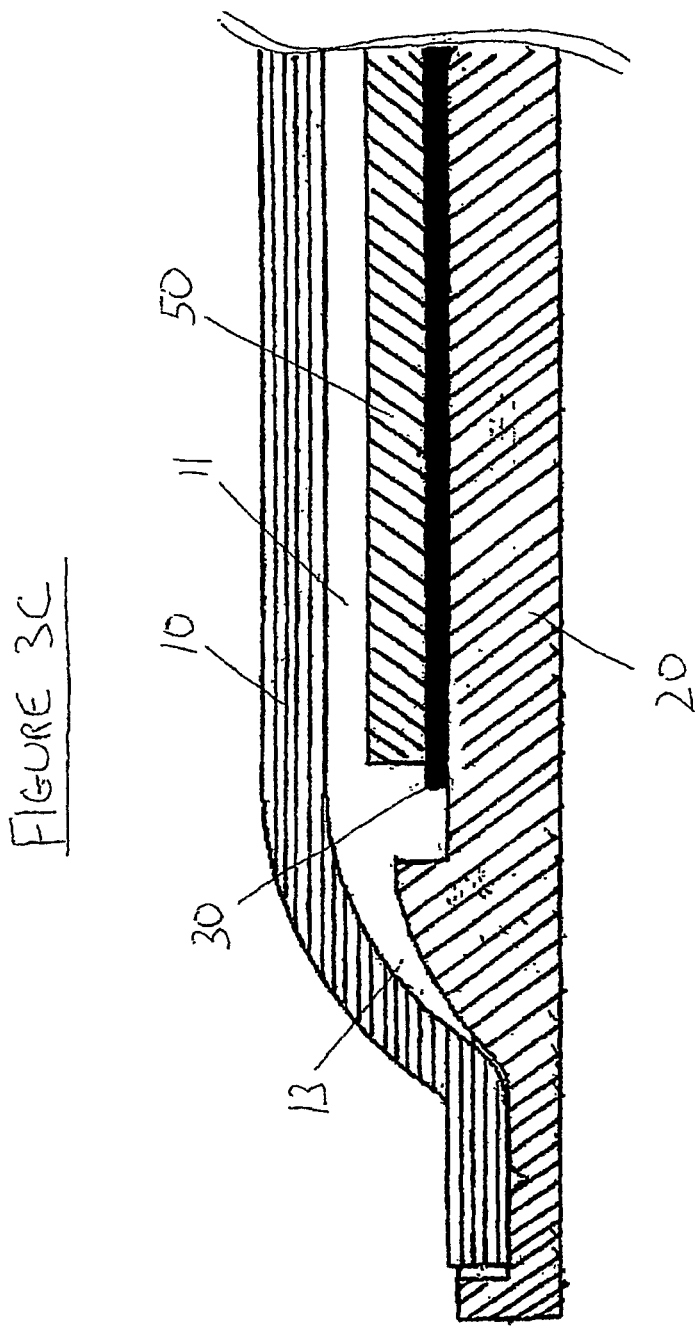

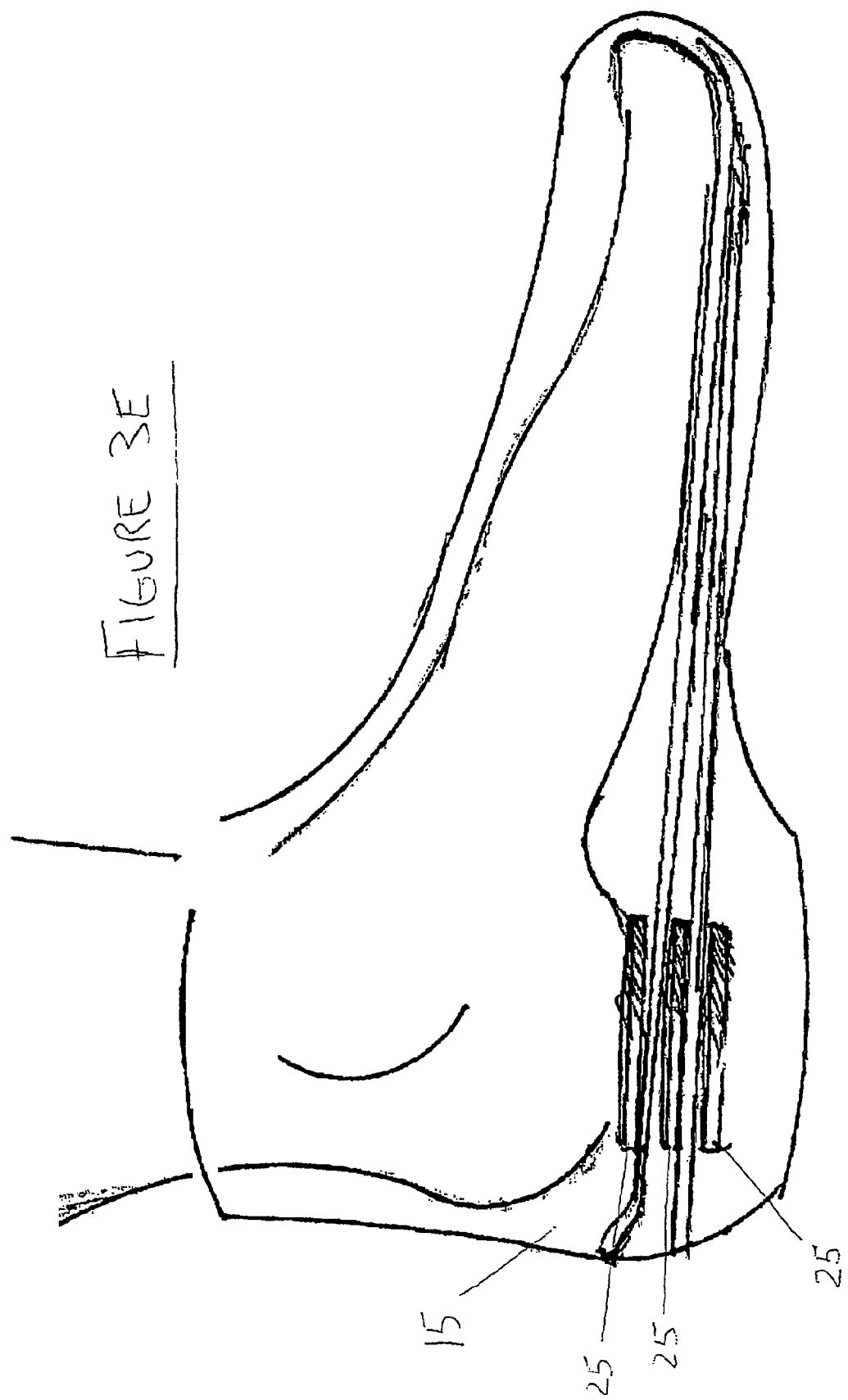

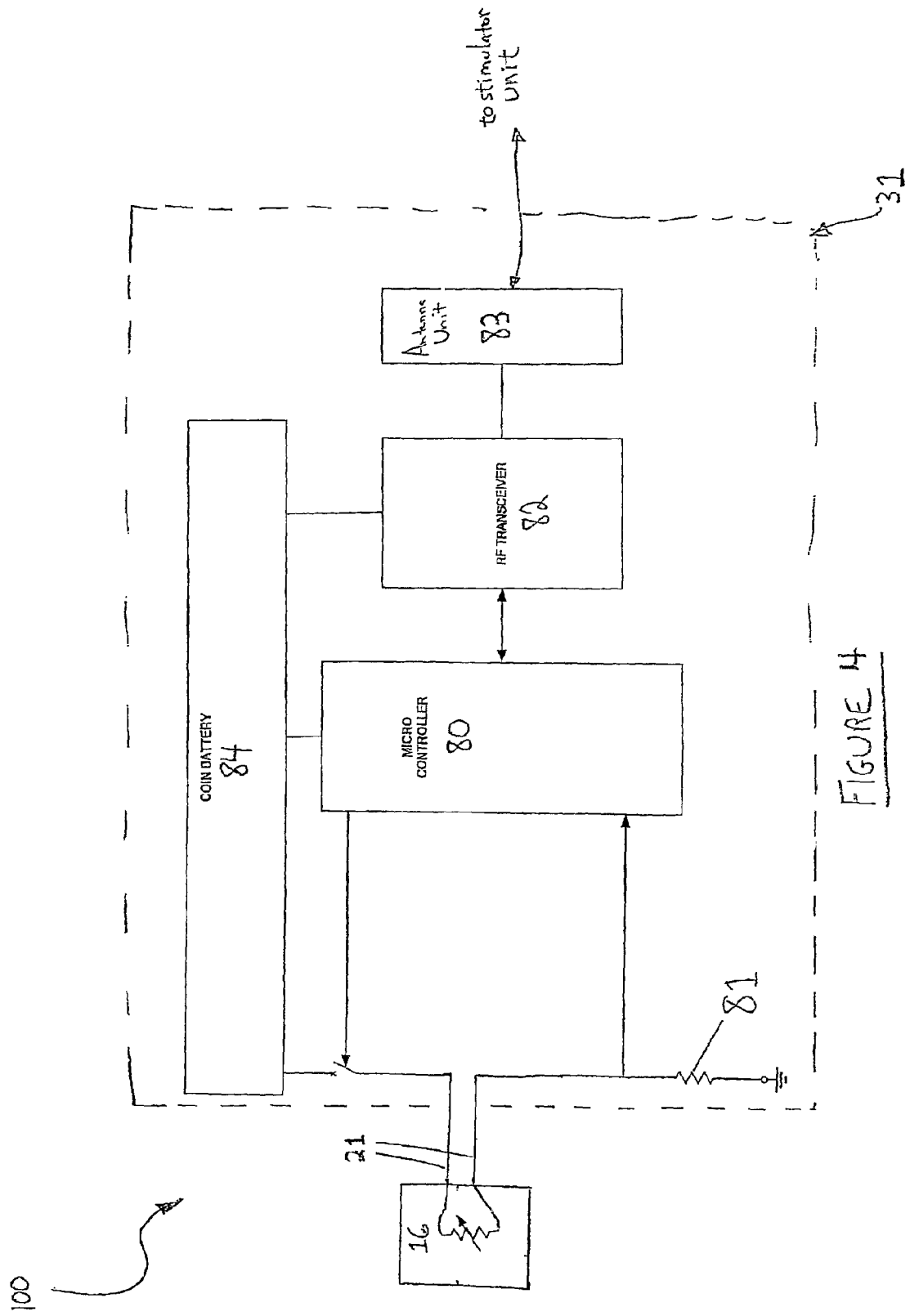

FUNCTIONAL ELECTRICAL STIMULATION SYSTEMS

CROSS-REFERENCE TO RELATED APPLICATIONS

This application is the U.S. national phase application of International Application No. PCT/IL2007/000531, filed May 1, 2007, entitled "Improved Functional Electrical Stimulation Systems," which claims the benefit of priority from U.S. Provisional Application Ser. No. 60/746,060, entitled "Foot Sensor—Dynamic Gait Tracking Algorithm," filed May 1, 2006, U.S. Provisional Patent Application Ser. No. 60/805,359, entitled "Foot Sensor Envelope," filed Jun. 21, 2006, and International Patent Application Serial No. PCT/IL2006/001326, entitled "Gait Modulation System and Method," filed Nov. 16, 2006.

International Application No. PCT/IL2006/001326 claims the benefit of priority from U.S. Provisional Application Ser. No. 60/736,858, entitled "Hybrid Orthosis; Foot Sensor; Electrode," filed Nov. 16, 2005, U.S. Non-Provisional patent application Ser. No. 11/380,430, entitled "Orthosis for a Gait Modulation System," filed Apr. 27, 2006, and U.S. Non-Provisional patent application Ser. No. 11/552,997, entitled "Sensor Device for Gait Enhancement," filed Oct. 26, 2006. U.S. Non-Provisional patent application Ser. No. 11/552,997 claims priority to U.S. Provisional Application Ser. No. 60/736,858, entitled "Hybrid Orthosis; Foot Sensor; Electrode," filed Nov. 16, 2005, U.S. Provisional Application Ser. No. 60/746,060, entitled "Foot Sensor—Dynamic Gait Tracking Algorithm," filed May 1, 2006, and U.S. Provisional Application Ser. No. 60/805,359, entitled "Foot Sensor Envelope," filed Jun. 21, 2006.

FIELD AND BACKGROUND OF THE INVENTION

The present invention relates to functional electrical stimulation (FES) devices and systems and, more particularly, to an improved envelope for force-sensitive resistors of such devices, and to FES devices and systems having improved monitoring, analysis, control, safety, energy conservation, and communication features.

It is known that various pathologies of the neuromuscular system due to disease or trauma to the central nervous system, such as stroke, spinal cord injury, head injury, cerebral palsy and multiple sclerosis, can impede proper limb functioning of the legs. Gait, the biomechanical description of walking, can suffer static and dynamic parameter variations due to neuromuscular impairments that cause non-symmetrical walking and reduced walking speed and stability, and often require increased energy consumption.

Drop foot describes the gait attributable to weak or uncoordinated activation of the ankle dorsi-flexors due to disease or trauma to the central nervous system. A patient suffering from drop foot tends to drag the foot during the swing phase of walking and usually try to compensate for this dragging by hiking the hip or swinging the affected leg in a circular motion. These patients tend to have impaired stability, are prone to frequent falls, and have walking movements that are unaesthetic and energy consuming.

It is known, however, that functional electrical stimulation (FES) can generally be used to activate the leg muscles of such patients. Precisely timed bursts of short electrical pulses are applied to motor nerves to generate muscle contractions, which are synchronized with the gait of the patient, so as to improve the leg function and enhance the gait. The timing of these pulses is critical, and must be synchronized with the gait. This is advantageously achieved by sensing gait events such as a foot-floor force reaction, using a force-sensitive resistor (FSR) disposed beneath the heel region of the patient, and transmitting the information to the stimulator unit.

The FSR sensor must be protected against water, humidity, dirt, and mechanical stress by means of a casing or envelope.

U.S. Pat. No. 6,507,757 to Swain, et al., discloses one typical foot sensor device of the prior art, in which a foot pressure switch, or sensor, is permanently disposed in the shoe of the affected leg. An electrical circuit is interrupted during the stance phase, when a significant weight is placed on the heel, and reconnects when the heel is lifted during the swing phase. Wires disposed under the clothing connect the sensor with an external stimulator unit that can be attached to the belt or kept in a pocket of the user. The stimulator unit is connected to the electrodes by additional electrical wires.

The cumbersome wires may be obviated by using a radio frequency (RF) system in which the foot sensor device and other components of the FES orthotic system communicate in a wireless fashion. However, the use of such an RF system necessitates integrating an RF transmitting unit, or head, within the foot sensor device. The RF communication with other components of the FES orthotic system must be robust and reliable, even in areas in which various types of wireless signals are prevalent, such as local area networks (LANs). The FES orthotic system must also be robust and reliable in areas in FES clinics and the like, in which one or more additional wireless FES systems may be operating simultaneously.

There is therefore a recognized need for, and it would be highly advantageous to have, an FES orthotic system for neuroprosthetic gait enhancement that overcomes the various deficiencies of the known systems. It would be of particular advantage for such a system that is robust and reliable, avoids the discomfort associated with various prior art stimulation devices, and is secured so as to operate in a safe and robust fashion.

SUMMARY OF THE INVENTION

According to the teachings of the present invention there is provided a gait modulation system utilizing functional electrical stimulation for improving lower-limb function of a patient having neuromuscular impairment of a lower limb, the gait modulation system including: (a) a sensor device including at least one sensor adapted for associating with at least one lower limb of the patient, the sensor for transducing at least one parameter related to a gait of the patient, so as to obtain gait data related to the gait, and (b) a muscle stimulator including: (i) an electrical stimulation circuit, the circuit adapted to supply an electrical stimulation output to an electrode array for performing functional electrical stimulation of at least one muscle of the lower limb, and (ii) a microprocessor, operatively connected to the at least one sensor, the microprocessor adapted for: receiving a stream of gait information based on the gait data; processing the gait information, and controlling the stimulation output based on the processing of the gait information, and wherein the microprocessor is further adapted to identify a failure in the stream of gait information, and to consequently control the electrical stimulation circuit to deliver a fail-safe stimulation output over at least a portion of a duration of the failure.

According to further features in the described preferred embodiments, the microprocessor is adapted to control the electrical stimulation circuit to provide the fail-safe stimulation output so as to reduce a falling risk of the patient.

According to still further features in the described preferred embodiments, associated with the microprocessor is a timing mechanism for timing the stimulation output based on the stream of gait information.

According to still further features in the described preferred embodiments, the microcontroller is adapted to make a prediction of a gait event of the patient based on the stream of gait information.

According to still further features in the described preferred embodiments, the microcontroller is adapted to control the electrical stimulation circuit to deliver the fail-safe stimulation output at a time based on the prediction of the gait event.

According to still further features in the described preferred embodiments, the prediction of the gait event is related to a prediction of a heel-contact event.

According to still further features in the described preferred embodiments, the prediction of the gait event is related to a prediction of a heel-off event.

According to still further features in the described preferred embodiments, the prediction of the gait event is related to a prediction of a SWING phase of the gait.

According to still further features in the described preferred embodiments, the prediction of the gait event is related to a prediction of a STANCE phase of the gait.

According to still further features in the described preferred embodiments, the failure includes a communication failure from a transmitting unit of the sensor device.

According to still further features in the described preferred embodiments, the communication failure is a radio frequency communication failure.

According to still further features in the described preferred embodiments, the sensor device further includes a microprocessor, electrically associated with the sensor, for receiving a signal pertaining to the parameter, and a transmitting unit for transmitting, in a wireless fashion, the gait information to a unit of the gait modulation system external to the sensor device.

According to another aspect of the present invention there is provided a gait modulation system utilizing functional electrical stimulation for improving lower-limb function of a patient having neuromuscular impairment of a lower limb, the gait modulation system including: (a) at least one sensor adapted for associating with at least one lower limb of the patient, the sensor for transducing at least one parameter related to a gait of the patient, so as to obtain gait data related to the gait; (b) a muscle stimulator including: (i) an electrical stimulation circuit, the circuit adapted to supply an electrical stimulation output to an electrode array for performing functional electrical stimulation of at least one muscle of the lower limb, and (c) a microprocessor, operatively connected to the at least one sensor, the microprocessor adapted for: receiving a signal containing gait information based on the gait data; processing the signal, and controlling the stimulation output based on the processing of the signal, wherein the sensor is a pressure sensor, and wherein the processing the signal includes: (i) calculating a dynamic range between maximal pressure values, and minimal pressure values on the pressure sensor, and (ii) calculating a high threshold and a low threshold based on the dynamic range, the low threshold for triggering on the electrical stimulation output, the high threshold for triggering off the electrical stimulation output.

According to still further features in the described preferred embodiments, the microprocessor is further adapted to detect a deviation from an ambulating mode.

According to still further features in the described preferred embodiments, the ambulating mode is a SWING state.

According to still further features in the described preferred embodiments, the ambulating mode is a STANCE state.

According to still further features in the described preferred embodiments, the microprocessor is further adapted to identify invalid peaks or valleys.

According to still further features in the described preferred embodiments, the microprocessor is further adapted to determine whether the patient is in a SWING, STANCE, SITTING, or STANDING state.

According to still further features in the described preferred embodiments, the microprocessor is further adapted to make a determination of an ambulating state of the patient, and to identify invalid peaks or valleys based on the determination.

According to still further features in the described preferred embodiments, the microprocessor is further adapted to utilize the dynamic range in identifying the invalid peaks or valleys.

According to still further features in the described preferred embodiments, the microprocessor has a plurality of different thresholds for determining peak validity or valley validity, the plurality of different thresholds based, at least in part, on an ambulating state of the patient.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like elements.

In the drawings:

FIG. 1 is a perspective view of the inventive sensor assembly;

FIG. 2 is a schematic, exploded view of the inventive sensor assembly, including an envelope cover, an envelope base, an FSR sensor, an electrical connection unit, and an absorbent protective layer for disposing on the FSR sensor;

FIG. 3C is a cross-sectional view of the inventive envelope showing the relative disposition of the envelope cover, envelope base, FSR sensor, and absorbent layer;

FIG. 3E is a schematic illustration of the inventive sensor assembly disposed within a conventional shoe;

FIG. 4 is a schematic electronic diagram of the inventive foot sensor device;

Figure 6:
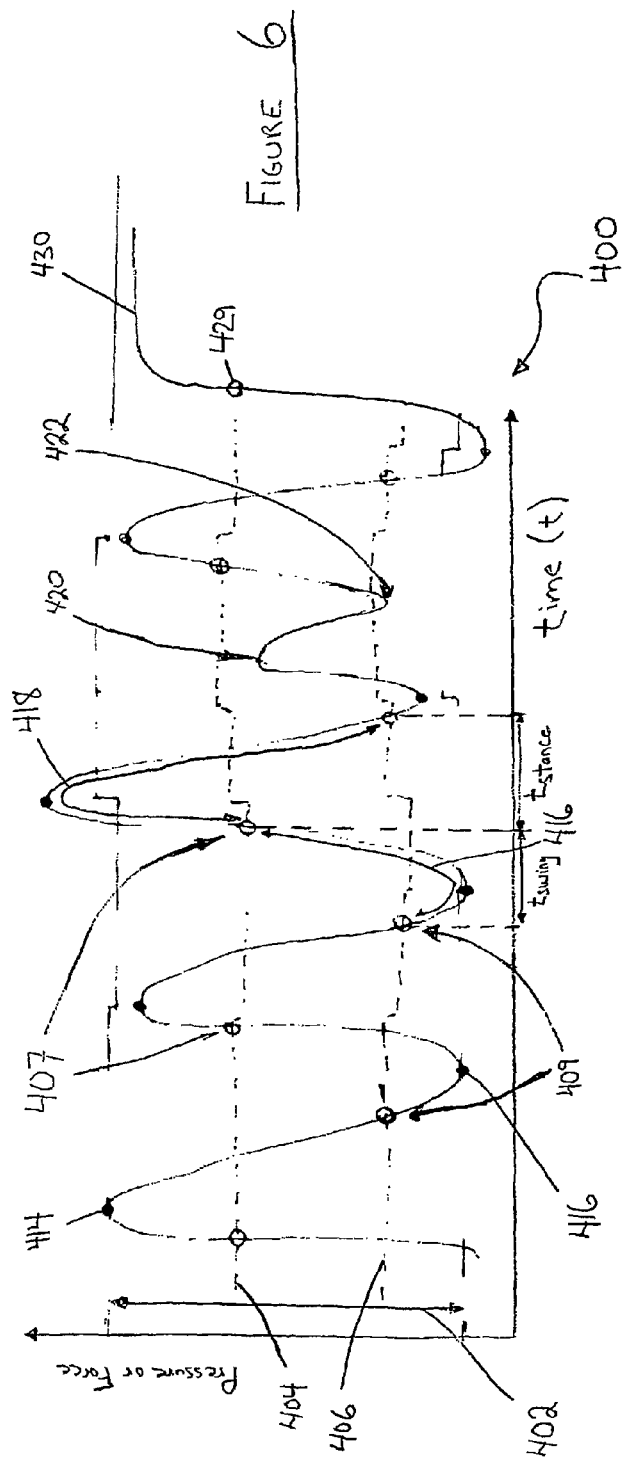
Figure 8:
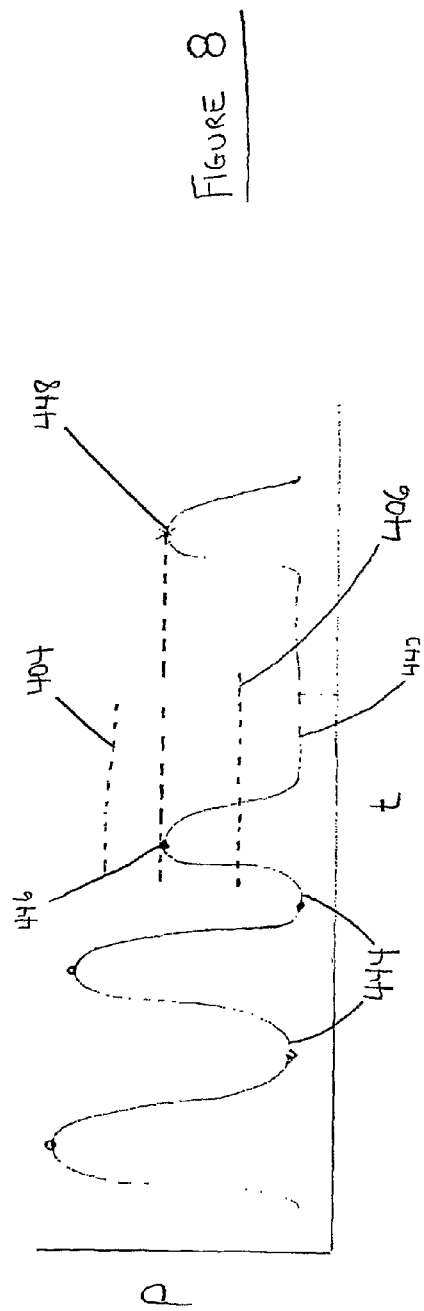
Figure 7:
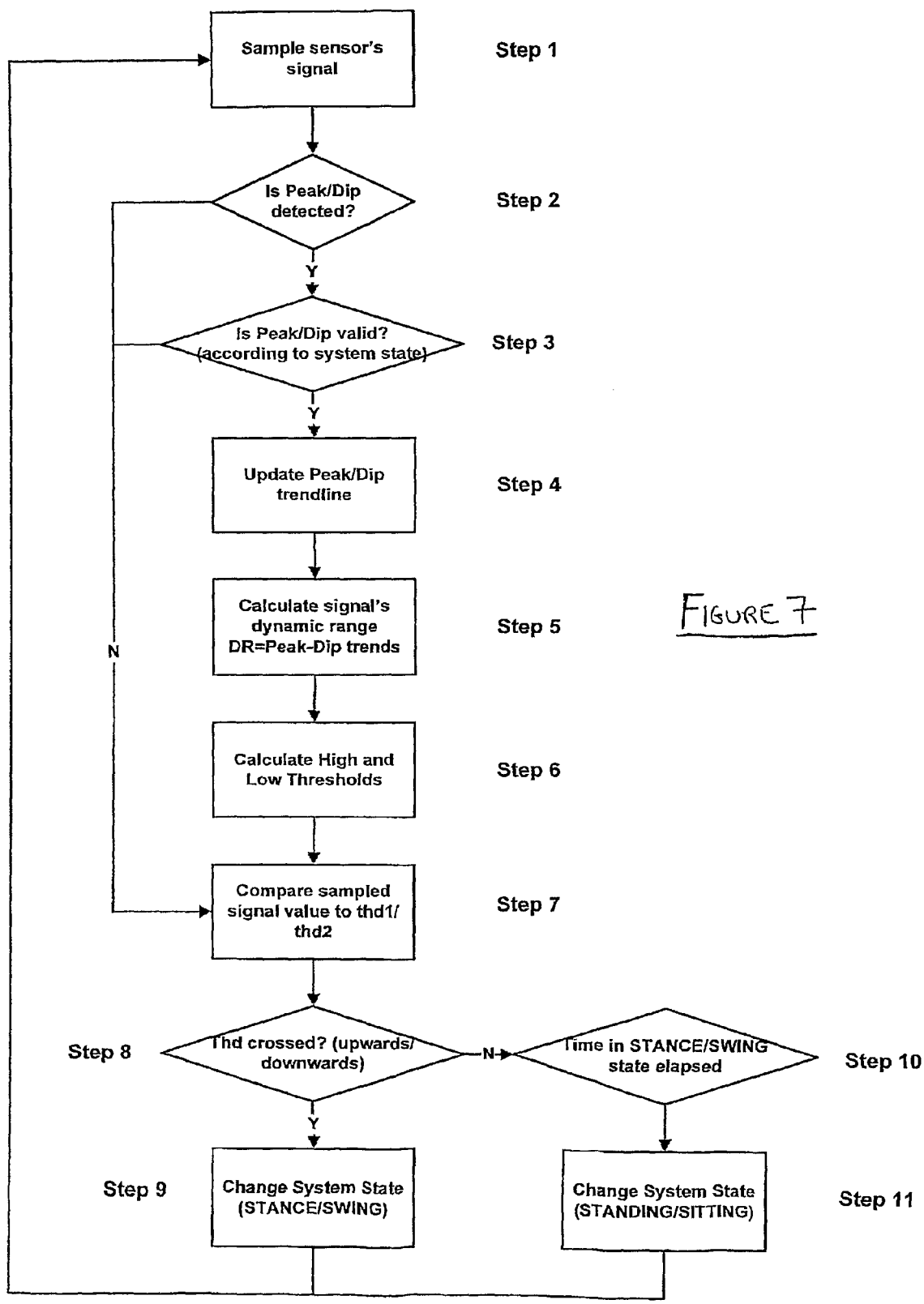
Figure 13:
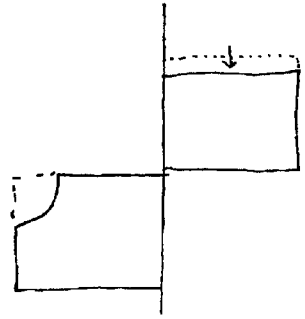
Figure 12:
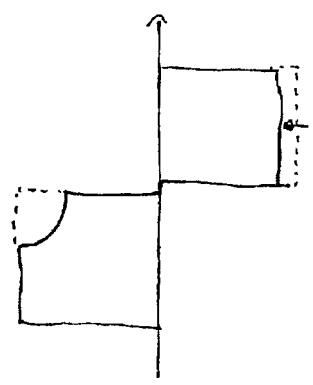
Figure 10:
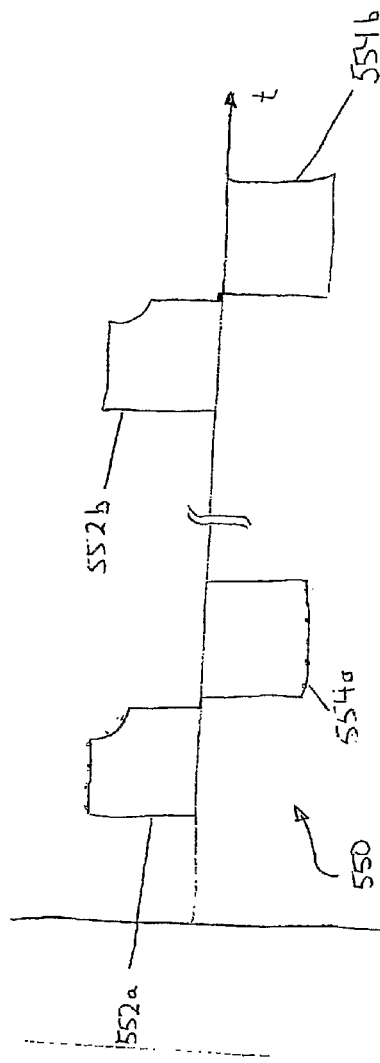
Figure 9:
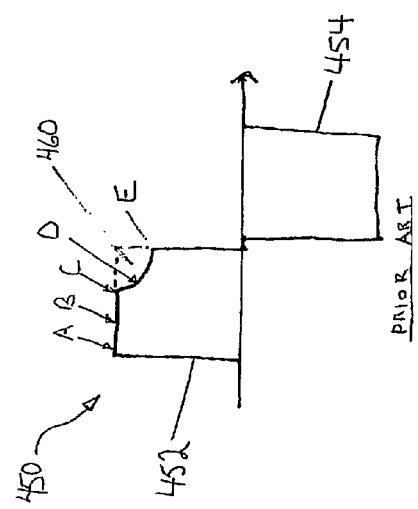
Figure 14:
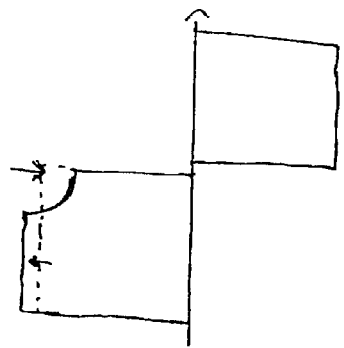
Figure 11:
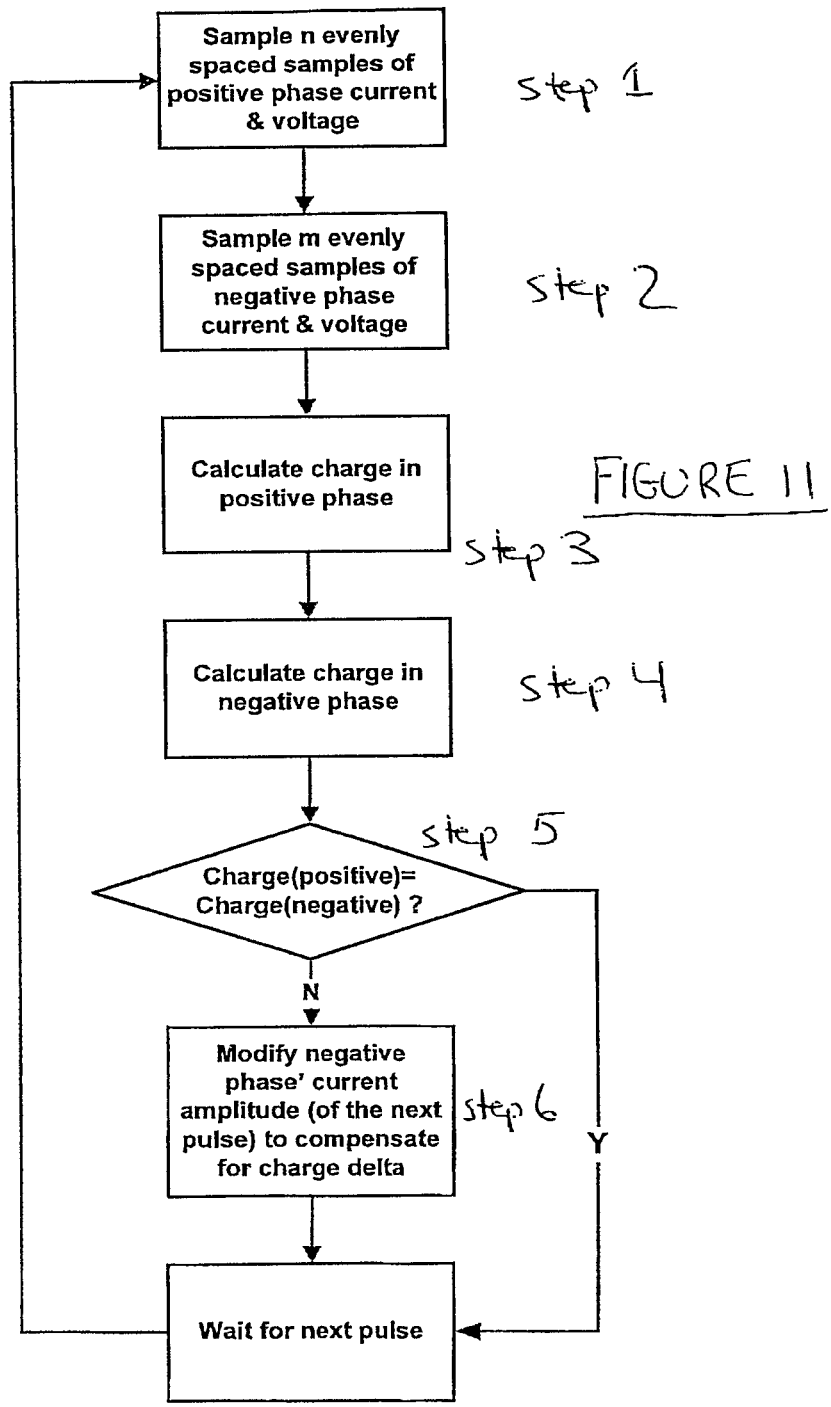

system, showing the internal workings of the foot sensor device, stimulator unit, and control unit, along with the communication between the components;

FIG. 6 is a schematic plot showing the pressure exerted on a pressure transducer as a function of time, during gait assisted by one embodiment of the system of the present invention;

FIG. 7 is an exemplary block diagram showing the logical sequence of analysis and control performed by a microcontroller unit of the present invention, based on data received from the pressure transducer;

FIG. 8 is a schematic, simplified plot showing the pressure exerted on the pressure sensor as a function of time, during gait assisted by a system of the present invention;

FIG. 9 is a schematic plot of current as a function of time for a bipolar stimulation pulse of the prior art;

FIG. 10 is a schematic plot of current as a function of time for successive bipolar stimulation pulses, showing exemplary sampling points;

FIG. 11 is a block diagram showing an exemplary embodiment of the inventive logical sequence of sampling, analysis and control performed by a microcontroller unit of the present invention;

FIG. 12 is a schematic plot showing one embodiment of charge balancing—reduced phase amplitude of a negative current phase;

FIG. 13 is a schematic plot showing another embodiment of charge balancing—reduced phase width (duration) of a negative current phase, and FIG. 14 is a schematic plot showing yet another embodiment of charge balancing—increased current to a greater than nominal level during a low-impedance section of the positive current phase.

DESCRIPTION OF THE PREFERRED EMBODIMENTS

The principles and operation of the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Various prior art sensor envelopes have appreciable deficiencies. One particular disadvantage is the lack of sufficient protection of the sensor by the sensor envelope. This lack of protection may cause an uncontrolled or uneven force distribution over the surface of the sensor, resulting in a relatively short life span for the sensor.

The FSR sensor assembly and envelope of the present invention is designed, preferably, for inserting under the inner sole (insole) of the shoe, typically beneath the heel. The protective casing is made of a cover and a base, with the sensor fitting therebetween. An additional piece of absorbent material is disposed between the cover and the FSR sensor. Typically, the absorbent material is adhered to the cover. The cover and base of the sensor casing can be connected to each other by ultrasonic welding, gluing, heat welding, RF welding or by pins. Various commercially-available force-sensitive resistor (FSR) sensors are suitable for use in conjunction with the inventive casing, including some FSRs manufactured by Interlink®, CUI®, Tekscan®, and Peratech®. The inventive casing can also be used with other types of sensors such as membrane switches, capacitance-based sensors and piezo-electric foils.

The envelope is preferably made of acetal [also known as polyacetal, polyoxymethylene (POM), or polyformaldehyde] or polypropylene, but other materials may be engineered to provide the requisite physical and mechanical properties, e.g., polyethylene terephthalate (PET).

FIG. 1 is a perspective view of one embodiment of a sensor assembly 25 of the present invention.

FIG. 2 is a schematic, exploded view of sensor assembly 25, including an envelope 5 having an envelope cover 10 and an envelope base 20; a force-sensitive resistor (FSR) sensor 30; an electrical connection unit 40; and an absorbent protective layer 50 for disposing on FSR sensor 30.

Base 20 forms sockets for FSR sensor 30 and for electrical connection unit 40. The sockets are preferably contoured to match the topographical features of the underside of the sensor and electrical connection unit. Base 20 has a circumferential rim for closely bounding FSR sensor 30, thereby determining the position of the sensor. Thus, the sockets enable precise, repeatable location of the sensor on the base.

Preferably, envelope base 20 is harder/less flexible than cover 10. This mechanical property reinforces the FSR sensor against bending forces, which can cause deviations in the sensor readings and can also cause excessive wear and damage to the sensor.

Figure 3A:
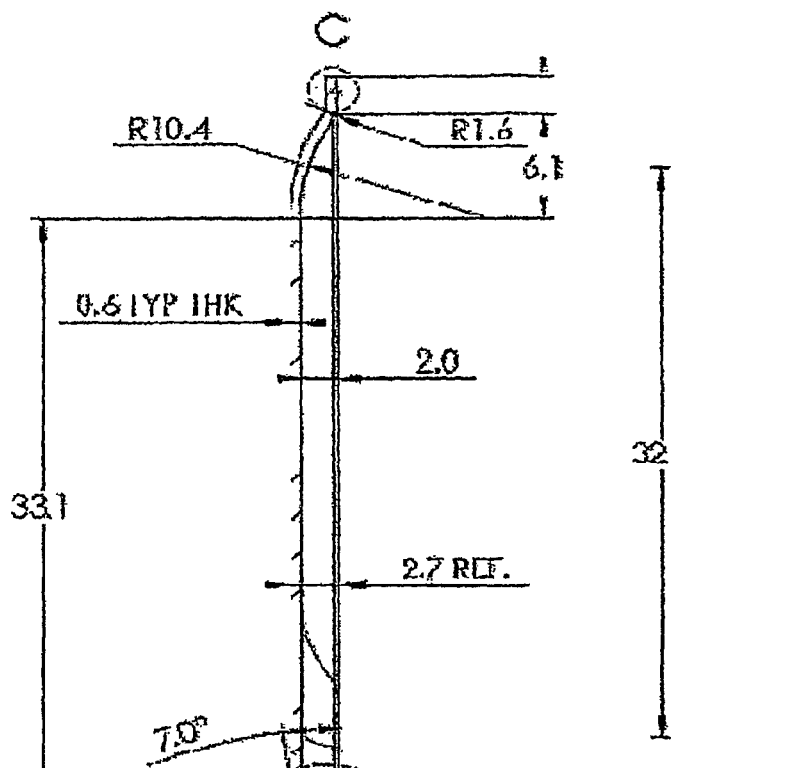
FIG. 3A is a cross-sectional view of inventive envelope cover.
Figure 3B:
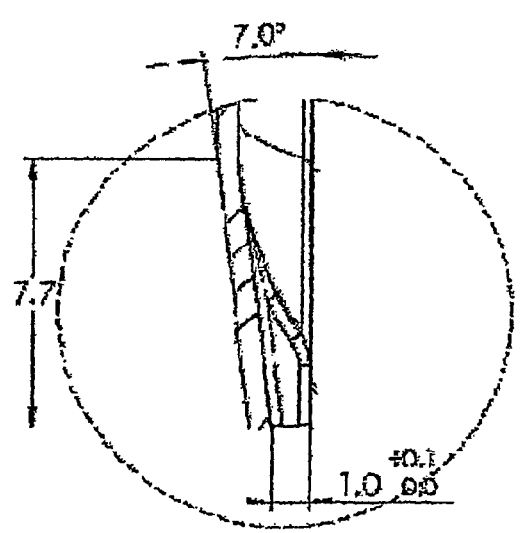
FIG. 3B is a magnified view of a portion of FIG. 3A.

FIG. 3A is a cross-sectional view of envelope cover 10; FIG. 3B is a magnified view of a portion of envelope cover 10 shown in FIG. 3A; FIG. 3C is a cross-sectional view of sensor assembly 25 showing the relative disposition of envelope cover 10, envelope base 20, FSR sensor 30, and absorbent layer 50.

It is evident from FIGS. 3A-3C that envelope cover 10 is supported around the circumference and largely unsupported towards the center. It is further evident from FIG. 3C that envelope cover 10, envelope base 20, and absorbent layer 50 are disposed such that a first void space 11 is situated between envelope cover 10 and absorbent layer 50, and such that a second void space 13 is situated between envelope cover 10 and envelope base 20. The flexibility of cover 10, along with the maneuverability provided by void spaces 11, 13, enables the cover to act like a membrane that collapses (bends) towards the center of the top face of FSR sensor 30, and transmits the pressure (force), via absorbent protective layer 50, thereto.

Preferably, the radius of cover 10 near the perimeter thereof is about 2-5 mm and more preferably, 3-4 mm.

The rims of cover 10 and base 20 are preferably contoured in complementary fashion. The closure of these rims is preferably made by ultrasonic welding. The bonding of the rims, coupled with the curved structure near the perimeter and the elevated rim thereunder, provide the requisite rigidity to the envelope. Consequently, routine forces exerted by the foot on the sensor will not collapse cover 10 near the envelope perimeter, and the collapsing is confined within the center area of the cover. The bonding of the rims actually generates a surface tension that allows the cover to collapse solely within that center area. This also eliminates distortion of the rims.

Absorbent protective layer 50, for disposing on FSR sensor 30, is preferably made of Poron®, or another flexible, high density, microcellular material that exhibits, over long-term use, good resistance to compression set (collapse), high resiliency, and good impact absorption.

The above-described features of the envelope and closure thereof allow more accurate, repeatable and reproducible collapse of cover 10 upon sensor 30. This permits repeatable readings of the sensor for a specific pressure (force). Perhaps more importantly, the above-described shape and structure eliminate or drastically reduce shear forces on sensor 30, and greatly contribute to the longevity of FSR sensor 30. The structure of the rims also improves the structural stability and durability of the envelope.

The sensor is anchored to the base of the envelope within a specific socket structure in base 20. In one embodiment, the wires are tightened by a metal crimp, which is positionally locked into the socket, thereby inhibiting movement of the sensor, as well as undesirable tension in the area of the wires (and especially to the welding points thereof) of electrical connection unit 40 as result of accidental pulling of the external wire.

Preferably, the sensor is attached to the shoe inner surface by loop and hook fasteners such as Velcro®. One fastening element is attached to the bottom of sensor base cover, and the complementary fastening element is attached to the shoe insole.

A graphical symbol of a foot is preferably provided on cover 10, so as to direct the user to properly align the FSR sensor device within the shoe.

The inventive envelope is easy and inexpensive to manufacture, and enables facile and reproducible assembly of the FSR sensor device.

Figure 3D:
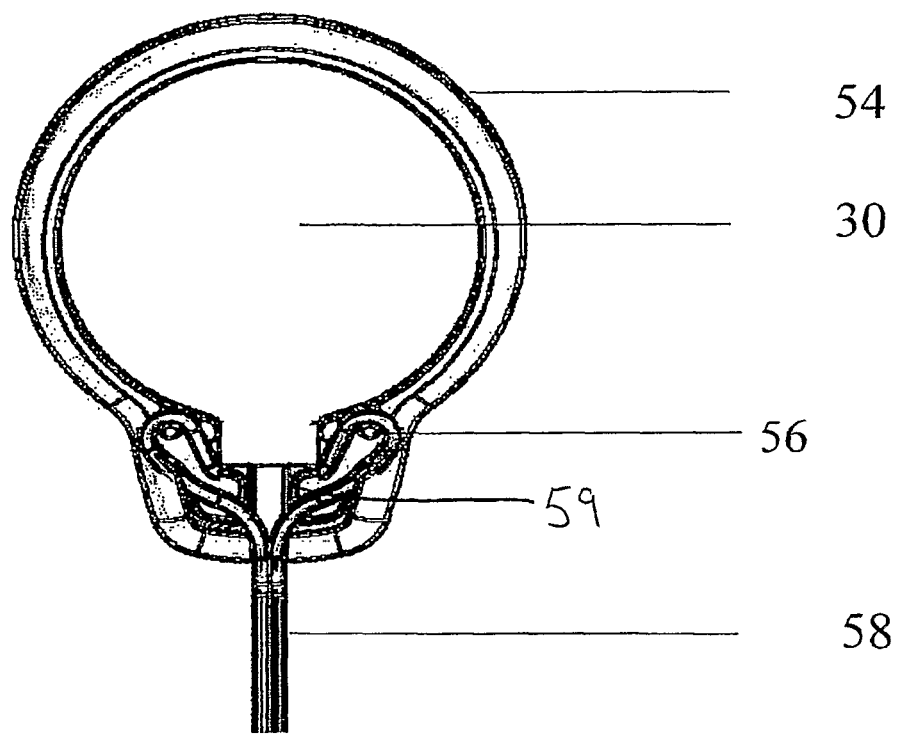
FIG. 3D is a schematic illustration of a preferred embodiment of the inventive envelope in which the envelope has a mechanism for advantageously securing FSR sensor to external wires.

FIG. 3D schematically illustrates a preferred embodiment of the present invention having an inventive mechanism for advantageously securing FSR sensor 30 to external wires 58. Wires 58 typically connect FSR sensor 30 with the head of the sensor device containing, inter alia, the microprocessor and radio frequency (RF) transceiver.

External wires 58 are anchored around protrusions such as protrusion 56, which juts out of a base 54 of FSR sensor 30. External wires 58 are wrapped around these protrusions in such a way that undesirable tension in the area of the wires (especially at the welding points 59) of the electrical connection is avoided. This anchoring mechanism enables the user to pull the envelope out of the shoe without inadvertently causing damage to the welding points in the area of the electrical connection.

Preferably, silicon is poured over the ends of wires 58 after wires 58 have been positioned, so as to maintain the positioning of the wires during assembly, as well as to further protect the welding area and to seal out water and dirt from the opening around the wire.

FIG. 3E is a schematic illustration of inventive sensor assembly 25 disposed within a conventional shoe or footwear 15. Sensor assembly 25 can be situated in various positions, e.g., under the foot/above the insole, between the insole and sole, and within the sole.

As used herein in the specification and in the claims section that follows, the term "footwear" refers to any kind of foot covering that a foot being covered presses down upon during gait, including, but not limited to, shoes, boots, sandals, socks, and stockings.

FIG. 4 is a schematic electronic diagram of inventive foot sensor device 100. Sensor element 16 is connected to, and preferably powered by, electronics or communication unit 31 by means of wiring 21. Communication unit 31 includes a digital circuit and microcontroller unit 80, a radio frequency (RF) transceiver 82, and an antenna unit 83 having a matching network for converting the signal from the wired medium to a wireless medium, and from the wireless medium to the wired medium.

The resistance of sensor element 16 changes with the force applied thereon. According to one embodiment of the present invention, foot sensor device 100 is equipped with a voltage divider consisting of sensor element 16 and a bias resistor 81 (preferably disposed in unit 30), in order to measure the resistance of sensor element 16. When a voltage is applied to the voltage divider, the voltage is divided according to the resistance ratio between sensor element 16 and bias resistor 81. This voltage is measured in order to assess the resistance of sensor element 16.

One skilled in the art will appreciate that there are numerous ways of measuring the resistance of sensor element 16.

Communication unit 31 is also equipped with a small coin battery 84 that provides power to microcontroller unit 80, RF transceiver 82, and sensor element 16.

Digital circuit and microcontroller unit 80 controls and monitors the operation of foot sensor device 100 and executes the various algorithms (e.g., gait detection, RF control, and power management algorithms) thereof. Preferably, microcontroller unit 80 communicates with RF transceiver 82 via a Serial Peripheral Interface (SPI).

Figure 5:
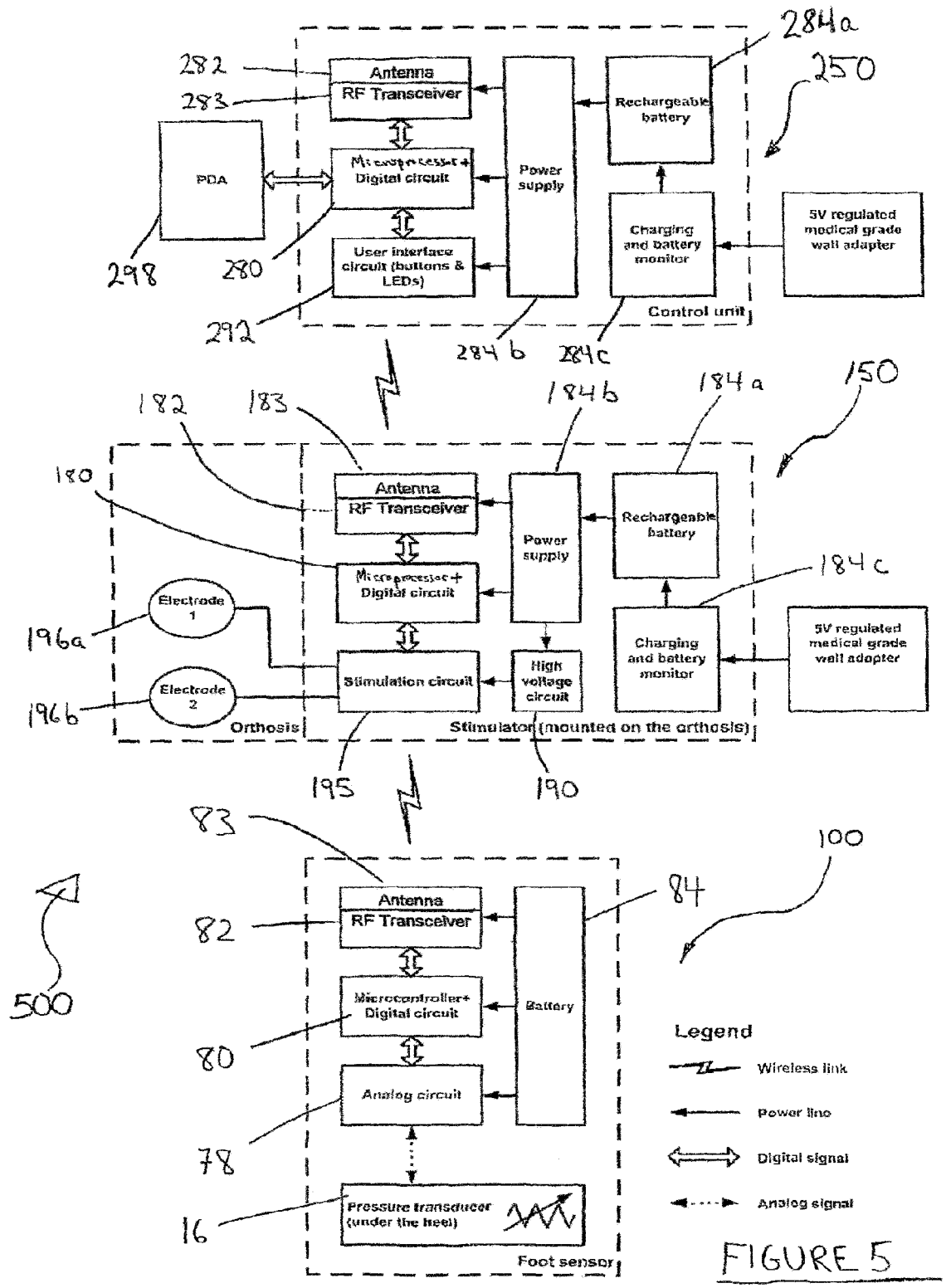
FIG. 5 is a schematic electronic diagram of one embodiment of the inventive functional electrical stimulation (FES)

FIG. 5 is a schematic electronic diagram of one embodiment of the inventive functional electrical stimulation (FES) system 500, showing the internal workings of foot sensor device 100, stimulator unit 150, and control unit 250, and the communication therebetween.

As above, foot sensor device 100 includes small coin battery 84 that provides power to microcontroller unit 80, RF transceiver 82, and sensor element 16. Coin battery 84 may also power an analog circuit 78 having sensor signal conditioning (such as amplification, filtering, and division) and an analog-to-digital signal converter.

Stimulator unit 150 typically includes an RF transceiver 182 having an antenna 183 having a matching network, a digital circuit and microcontroller unit 180, and a stimulation circuit 195, all powered by a power supply 184b. Stimulation circuit 195 typically receives power from power supply 184b via high voltage circuit 190.

Power supply 184b may be powered by a battery such as rechargeable battery 184a. A charging and battery monitor 184c is advantageously associated with rechargeable battery 184a, and interfaces with an external power supply, such as a regulated, preferably medical-grade, wall adapter.

By means of antenna 83 of foot sensor device 100 and antenna 183 of stimulator unit 150, RF transceiver 82 communicates with RF transceiver 182 of stimulator unit 150. RF transceiver 182 transmits digital information to and receives digital information from digital circuit and microcontroller unit 180. Similarly, microcontroller unit 180 and stimulation circuit 195 exchange digital information. Stimulation circuit 195, based on digital information from microcontroller unit 180, and powered by high voltage circuit 190, is configured to deliver electrical stimulation pulses to the patient by means of electrodes 196a, 196b disposed in the orthosis unit.

Control unit 250 typically includes an RF transceiver 282 having an antenna 283 having a matching network, a digital circuit and microcontroller unit 280, and a user interface circuit 192, all powered by a power supply 284b.

Power supply 284b may be powered by a battery such as rechargeable battery 284a. A charging and battery monitor 284c is advantageously associated with rechargeable battery 284a, and interfaces with an external power supply, such as a regulated, preferably medical-grade, wall adapter.

By means of antenna 183 of stimulator unit 150 and antenna 283 of control unit 250, RF transceiver 182 communicates with RF transceiver 282 of control unit 250. RF transceiver 282 transmits digital information to and receives digital information from digital circuit and microcontroller unit 280. Similarly, microcontroller unit 280 and user interface circuit 192 exchange digital information. For example, user preferences for various operating parameters can be communicated from user interface circuit 192 to microcontroller unit 280. Microcontroller unit 280 may be adapted to provide user interface circuit 192 with display information, including pertaining to stimulation parameters.

As is known in the art, PDAs such as PDA 450 are small, hand-held portable computers having a Central Processing Unit (CPU) and electronic memory, and are generally used for storing and organizing information and for providing tools for everyday tasks. The PDA may advantageously be operated by the Windows Mobile 5 software of Microsoft®. PDA 450 preferably has a database containing a gait log and various personal parameters of the patient, and is programmed to configure the stimulation parameters of the electrical stimulation system.

PDA 450 and control unit 250 are preferably in digital and electrical communication, such that the orthosis system can be configured on-line by the clinician during actual usage of the orthosis by the patient. In this arrangement, control unit 250 actually serves as the transmitter of PDA 450, enabling PDA 450, via control unit 250, to communicate with and command the other components of the electrical stimulation system.

RF Protocol—Fast Wireless Link Failure Identification (FLFI) Algorithm and Response A microprocessor within the inventive system, by means of the RF protocol software, implements a method for a Fast wireless Link Failure Identification (FLFI). If failure is identified, the system provides a fail-safe stimulation to promote gait stability.

As used herein in the specification and in the claims section that follows, the term "stance time" refers to the time differential between a heel-off event and the previous heel-contact event.

As used herein in the specification and in the claims section that follows, the term "swing time" refers to the time differential between a heel-contact event and the previous heel-off event.

When, for whatever reason, a 'heel-off' event is not identified immediately after receiving or identifying a 'heel-contact' event, the situation of the user may be precarious: the stimulator resumes its 'heel-contact' activity and does not deliver stimulation, which may cause the patient to lose balance, to stumble, or even to fall.

In order to reduce this risk, the system (e.g., microcontroller unit 80 of foot sensor device 100 or in other possible embodiments, microcontroller unit 180 of stimulator unit 150) frequently or substantially constantly calculates, and/or monitors, the last or average stance time of the patient. From the average stance time, microcontroller unit 80 calculates a 'keep-alive' duration, which is longer than the stance time. Preferably, the 'keep-alive' duration is at least one hundredth of a second, more preferably, at least one tenth of a second, most preferably, at least 0.8 seconds. As a function of stance time, preferably, the 'keep-alive' duration is at least 0.01 times the stance time, preferably, at least 0.1 times the stance time, and most preferably, at least slightly longer than the stance time.

Microcontroller unit 80 transmits this 'keep-alive' duration along with any heel event, to stimulator unit 150.

If, after detecting a heel-contact event, microcontroller unit 80 does not detect a heel-off condition, microcontroller unit 80 transmits a 'keep-alive' message after the 'keep-alive' duration, so that stimulator unit 150 is aware that the link with foot sensor device 100 is functional, but that there are no events to report.

If, on the other hand, the RF link is blocked right after transmitting the last heel-contact event (and the 'keep-alive' duration thereof), microcontroller unit 180 recognizes that the link with foot sensor device 100 is not functional (no event message, nor 'keep-alive' message), and in the absence of gait event information, commands stimulation circuit 195 to apply a fail-safe stimulation for a pre-defined period of time. The fail-safe stimulation is delivered to the tissue slightly after the heel-off event should have been received, had no RF blocking occurred, since the 'keep-alive' duration is calculated based on the stance duration. This fail-safe stimulation helps the patient with dorsiflexion and reduces the risk of falling by substantially imitating the function of a mechanical orthosis (ankle-foot orthosis).

RF Protocol—Range-Dependent Registration

Referring again to FIG. 5, FES system 500 employs a registration mechanism that enables several such systems to simultaneously operate in the same frequency channel. The registration is based on a unique identifier, preferably incorporated into the hardware of control unit 250, which serves as a digital 'family name' for all of the components of FES system 500: foot sensor device 100, stimulator unit 150, and control unit 250.

Each transmission of each system component 100, 150, 250 preferably carries this identifier as a part of the payload. When one of transceivers 82, 182, 282 receives the transmitted message, the transceiver first verifies that the transmitter belongs (is registered) to the same family, and only after verification proceeds to handle the transmitted data.

The registration process also defines how the new component is introduced into an existing system, for example, as a replacement part. In this case, the end user moves the system to 'registration mode' by pressing a pre-defined key sequence on control unit 250. Preferably, this key sequence is the same, regardless of the new component that is being introduced (registered) to FES system 500.

Foot Sensor—Dynamic Gait Tracking Algorithm

A microcontroller unit such as microcontroller unit 80 of foot sensor device 100 (or another microcontroller unit within the system, such as microcontroller unit 180 of stimulator unit 150) is preferably configured to implement a 'Dynamic Gait Tracking' algorithm. This algorithm is designed to handle variable sensor response arising from various sources, including:

variations between sensors;
variations in signal level and pattern due to variable patient weight;
variations in signal level and pattern due to differences in weight bearing form over the sensor;
variations in signal level and pattern due to changes in sensor characteristics caused by the operation environment (sensor heats up within a shoe);
variations in signal level and pattern due to changes in sensor characteristics caused by prolonged use;
variations of forces over the sensor due to differences between individual shoes and differences between individual insoles.

FIG. 6 is a schematic plot 400 showing, on the Y-axis, a magnitude or amplitude of pressure (or force) exerted on a pressure transducer (such as pressure transducer 16 shown in FIG. 5) as a function of time, during gait assisted by an FES system of the present invention. The plot has a calculated dynamic range 402, which is a smoothed and or averaged differential between maximal or peak pressure values, and adjacent minimal or valley pressure values on pressure transducer 16. From the dynamic range are calculated a high threshold 404 and a low threshold 406, which serve as references for determining heel-contact events and heel-off events, respectively.

FIG. 6 will be more readily understood after describing FIG. 7, which is an exemplary block diagram showing the logical sequence of analysis and control performed by microcontroller unit 80 of foot sensor device 100, based on data received from pressure transducer 16.

In step 1, microcontroller unit 80 samples the signal of pressure transducer 16. If a peak or valley is detected (step 2), microcontroller unit 80 determines whether the peak or valley is a valid peak or valley, or an invalid peak or valley (step 3). If the peak or valley is found to be valid, the relevant trendline is updated (step 4), and the new dynamic range is calculated (step 5). As described hereinabove, high threshold 404 and low threshold 406 are recalculated based on the new dynamic range (step 6).

Next, the signal sampled in step 1 is compared with high threshold 404 and low threshold 406 (step 7), and microcontroller unit 80 determines (using signal data from at least one previous sampling) whether high threshold 404 or low threshold 406 has been crossed (step 8). If either threshold has been crossed, microcontroller unit 80 effects a change in the state of the system (step 9), from a STANCE state to a SWING state, triggering electrical stimulation, or from a SWING state to a STANCE state, triggering a cutting off of the stimulation. The logical sequence of analysis and control returns to step 1, in which microcontroller unit 80 again samples the signal of pressure transducer 16.

In the routine event that a peak or valley is not detected (step 2), or that the peak or valley detected is not valid (step 3), the logical sequence preferably proceeds directly to step 7, in which the sampled signal is compared with high threshold 404 and low threshold 406.

If microcontroller unit 80 determines, in step 8, that high threshold 404 or low threshold 406 has not been crossed, the time elapsed within the current system state (STANCE or SWING) is evaluated (step 10). If the time elapsed exceeds a particular value, e.g., a calculated value based on the average stance/swing period, microcontroller unit 80 determines (step 1) that the user of the FES system is now in a STANDING state or in a SITTING state. The particular value may be an absolute value, a calculated value based on the average stance/swing period, or based on a previous stance/swing period or periods, a function of the elapsed time of the previous peak or peaks, and/or a function of another gait parameter.

The logical sequence of analysis and control returns to step 1, in which microcontroller unit 80 again samples the signal of pressure transducer 16.

Referring back to FIG. 6, each of points 407 represents a crossing of high threshold 404; each of points 409 represents a crossing of low threshold 406. After determining that high threshold 404 has been crossed, microcontroller unit 80 effects a change in the state of the system from a SWING state 416 to a STANCE state 418. Similarly, upon determining that low threshold 406 has been crossed, microcontroller unit 80 effects a change in the state of the system from a STANCE state to a SWING state. Typically, stimulation circuit 195 is commanded to provide stimulation current during the course of SWING state 416.

Peak 430 is characteristically long with respect to typical STANCE peaks during gait. If the time elapsed since crossing a high threshold point 429 exceeds a particular value (without crossing low threshold 406), microcontroller unit 80 determines that the state of the user of the FES system has changed from a STANCE state to a STANDING state. As in the parallel case described hereinabove, the particular value may be an absolute value, a calculated value based on the average stance/swing period or based on a previous stance/swing period or periods, a function of the elapsed time of the previous peak or peaks, and/or a function of another gait parameter.

Similarly, if the time elapsed for a particular valley exceeds a pre-determined value, microcontroller unit 80 determines that the state of the user has changed from a SWING state to a SITTING state.

As described briefly hereinabove, microcontroller unit 80 determines whether a peak or valley is valid or invalid. Peak 414 is an example of a valid peak; valley 416 is an example of a valid valley.

An invalid peak, such as invalid peak 420, has an amplitude that is less than a particular level. This pre-determined level is, at least in part, a function of the dynamic range. Thus, by way of example, a peak may be considered invalid if the peak amplitude is less than a pre-determined percentage of the dynamic range. Similarly, a valley may be an invalid valley such as invalid valley 420, if the amplitude of the valley (i.e., the drop in pressure from the previous peak to the valley is less than a pre-determined percentage of the dynamic range.

Since invalid peaks and valleys are not entered into the calculation of the trendlines, the dynamic range remains substantially unchanged. Consequently, these invalid peaks and valleys do not influence the determination of high threshold 404 and low threshold 406.

With reference now to FIG. 8, FIG. 8 is a schematic, simplified plot showing the pressure exerted on the pressure transducer as a function of time, during gait assisted by a system of the present invention. The time elapsed for valley 442 greatly exceeds the time elapsed for typical valleys such as valleys 444. Accordingly, microcontroller unit 80 determines that the state of the user has changed from a SWING state to a SITTING state.

Similarly, if the time elapsed from the start of a peak exceeds the time elapsed for typical peaks (such as peak 430 in FIG. 6) by a pre-calculated or predicted value, microcontroller unit 80 determines that the state of the user has changed from STANCE to STANDING.

In a preferred embodiment of the present invention, the determination of peak and valley validity is additionally and preferably dependent on the gait state. Each gait state preferably has an individual, dynamic threshold—typically a percentage or other function of the dynamic range—for determining peak and valley validity. This threshold should not to be confused with the heel-off and heel-contact thresholds described hereinabove.

By way of example, the inventors have discovered that while in a SITTING state, a relatively high threshold reduces the occurrence of false stimulation. By means of such a high threshold, the system is largely impervious to the effects of weight shifting while sitting, because the relatively low peaks generated by such weight shifting are considered invalid, and are not 'entered' into the trendline calculation. Consequently, these false gait peaks do not "pull" downward the peak trendline, do not decrease the dynamic range, and do not falsely sensitize the stimulation threshold (low threshold). As a result, the user enjoys a more quiet sitting, in which false stimulation while sitting is appreciably reduced.

Similarly, during standing, the system is largely impervious to the effects of weight shifting, because the relatively low amplitude of the valleys generated by such weight shifting are considered invalid, and are not 'entered' into the trendline calculation. Consequently, these false gait valleys do not "pull" upward the valley trendline, do not decrease the dynamic range, and do not falsely sensitize the stimulation threshold (low threshold). As a result, a standing user who shifts his weight from time to time is less inconvenienced by false stimulation, which can be appreciably reduced.

Typical validity conditions for each of the four states—STANCE; STANDING; SWING, and SITTING—are provided below:

STANCE state: valid peak amplitude≥25%·dynamic range
STANDING state: valid peak amplitude≥62.5%·dynamic range
SWING state: valid valley amplitude≥25%·dynamic range
SITTING state: valid valley amplitude≥50%·dynamic range Thus, it is observed in FIG. 8 that while peak 446 and peak 448 are of substantially equal amplitude, peak 446 is considered to be a valid peak, while peak 448 is considered to be an invalid peak. Peak 446 belongs to the SWING state, whereas peak 448 belongs to the SITTING state.

Foot Sensor—Dynamic Gait Tracking Algorithm

The software preferably samples the signals before and during each of the stimulation pulses. The monitored parameters and conditions may include:

Body leakage current (hazard)
Pulse balance monitoring and correction (hazard)
Tissue impedance estimation and electrode disconnection identification
Pulse over current (hazard)
Pulse over duration (hazard)

With reference now to FIG. 9, FIG. 9 is a schematic plot of current as a function of time, for a bipolar stimulation pulse 450 of the prior art. Stimulation pulse 450 is substantially a square wave having a positive current phase 452 and a negative current phase 454.

It is known that over the course of applying a large plurality of stimulation signals to the tissue of the user, an imbalance between the charge delivered in the positive current phases and the charge delivered in the negative current phases can cause irritation to the tissue and discomfort to the user. It is also known that delivering current to the tissue so as to effectively cause FES typically leads to such a disadvantageous imbalance.

Without wishing to be limited by theory, the inventors believe that this phenomenon is related to the dynamic impedance behavior of the tissue. Initially, the impedance of the tissue is relatively low, such that the requisite current can be delivered at an acceptably low voltage. With time, however, the impedance of the tissue may increase substantially, and to deliver constant current (so as to obtain a square wave), the voltage must be increased. According to Ohm's Law:

$$V = I \cdot Z$$

where V is the potential difference between two points in the tissue that include an impedance Z, and I is the current flowing through the impedance. Thus, the voltage is increased substantially proportionally to the impedance or resistance.

However, the voltage applied to the human body generally cannot be raised above a certain level, e.g., 120 Volts, consequently, as the impedance builds up, the current delivered may be limited—even severely limited—by the ceiling voltage.

Referring again to FIG. 9, stimulator devices of the prior art are often constant voltage devices. Thus, at the beginning of the signal (point A), when the impedance of the tissue is relatively low, positive current phase 452 is substantially a square wave. At point B, the impedance of the tissue has increased, but the source voltage still exceeds the multiplication product I·Z. At point C, however, the impedance of the tissue has increased to the point that the source voltage exactly equals the multiplication product I·Z. Thus, a further build-up in the impedance of the tissue forces the current delivered to drop (point D), monotonically, until positive current phase 452 is completed (point E).

Positive current phase 452 is not, therefore, a perfect square wave, and the total charge delivered is substantially less than the calculated total current based on the square wave model. Consequently, the total charge delivered in negative current phase 454 tends to exceed the total charge delivered in positive current phase 452, which often results in skin irritation in the area through which the current is passed.

Such stimulator devices of the prior art are of further disadvantage in that the use of constant voltage near the beginning of positive current phase 452 can be wasteful from an energy standpoint.

The method and system of the present invention perform digital pulse balancing, in real time, on the bipolar stimulation signal, so as to greatly improve current balance. Referring collectively to FIGS. 5 and 10 along with FIG. 11, FIG. 11 is a block diagram showing an exemplary embodiment of the inventive logical sequence of sampling, analysis and control performed by a microcontroller unit of the present invention. The sequence is designed to adjust or balance a bipolar digital stimulation current pulse 550 delivered by stimulation circuit 195.

In step 1, a positive current phase 552a of bipolar current pulse 550 is sampled/monitored over n preferably evenly-spaced sample points. Preferably, the voltage is also sampled/monitored, and the impedance is calculated. The sampling/monitoring is preferably conducted at least 3 times, and more preferably, at least 5 times, over the duration of positive current phase 552a. In terms of timing, sampling is preferably conducted at least once every 10 microseconds over the duration of positive current phase 552a.

In step 2, a negative current phase 554a of bipolar current pulse 550 is sampled/monitored over m preferably evenly-spaced sample points. Preferably, the voltage is also sampled/monitored.

The charge in positive phase 552a and the charge in negative phase 554a are calculated based on the sampling points, and in some cases, the sampling times (steps 3 and 4), and these charges are then compared (step 5) to see if they are substantially equal, or that the charge differential is relatively small. If so, no balancing action is required, and the system waits for the next stimulation pulse.

If the charge differential is significant, pulse balancing is performed (step 6), preferably on at least one of positive current phase 552b and negative current phase 554b of the next current pulse. The pulse balancing is performed by controlling at least one pulse parameter so as to improve charge balance between positive current phase 552a and a negative current phase such as negative current phase 554b.

Various pulse parameters may be controlled to improve the charge balancing, including at least one of the following: current (positive phase or negative phase), positive current phase width, and negative current phase width. Preferably, charge balancing is performed by controlling a pulse parameter of the negative phase.

Some exemplary embodiments of the charge balancing are provided in FIG. 12—reduced phase amplitude of a negative current phase; FIG. 13—reduced phase width (duration) of a negative current phase; and FIG. 14: increased current to a greater than nominal level, at least during a portion of the positive current phase.

Preferably, at low impedance levels, the voltage is adjusted to achieve substantially the minimum voltage satisfying Ohm's Law, so as to conserve energy/battery power.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An apparatus, comprising:
a sensor configured to produce a gait signal as a function of time, the gait signal associated with a force exerted by a lower limb of a patient; and
a processor configured to calculate a first threshold and a second threshold, the first threshold calculated based on a dynamic range of the gait signal, the first threshold associated with a first gait event, the second threshold calculated based on the dynamic range of the gait signal, the second threshold associated with a second gait event,
the processor configured to produce a first signal when the gait signal crosses the first threshold, the processor configured to produce a second signal when the gait signal crosses the second threshold.

2. The apparatus of claim 1, further comprising:
a wireless transmitter configured to transmit at least one of the first signal or the second signal to a stimulation system, the stimulation system configured to initiate an electronic stimulation when the first signal is received, the stimulation system configured to terminate the electronic stimulation when the second signal is received.

3. The apparatus of claim 1, wherein the processor is configured to determine based on the gait signal whether the patient is walking, standing or sitting.

4. The apparatus of claim 1, wherein:
the gait signal includes a plurality of maximums and a plurality of minimums; and
the processor is configured to identify a first maximum from the plurality of maximums as being unrelated to ambulatory movement of the patient, the processor configured to calculate the dynamic range based on the plurality of maximums and the plurality of minimums, exclusive of the first maximum.

5. The apparatus of claim 4, wherein the first maximum occurs within a time period during which the patient is standing.

6. The apparatus of claim 1, wherein:
the gait signal includes a plurality of maximums and a plurality of minimums; and
the processor is configured to identify a first minimum from the plurality of minimums as being unrelated to ambulatory movement of the patient, the processor configured to calculate the dynamic range based on the plurality of maximums and the plurality of minimums, exclusive of the first minimum.

7. The apparatus of claim 6, wherein the first minimum occurs within a time period during which the patient is sitting.

8. The apparatus of claim 1, wherein:
the first gait event is a stance event; and
the second gait event is a swing event, the processor configured to produce a third signal after the first signal when the gait signal does not cross the second threshold within a predetermined time period.

9. An apparatus, comprising:
a sensor configured to produce a gait signal as a function of time, the gait signal associated with a force exerted by a lower limb of a patient; and
a processor configured to calculate, based on the gait signal, a first threshold and a second threshold, the first threshold associated with a first gait event, the second threshold associated with a second gait event,
the processor configured to produce a first signal when the gait signal crosses the first threshold at a first time, the processor configured to produce a second signal at a second time, the second time occurring a predetermined time period after the first time.

10. The apparatus of claim 9, wherein the processor is configured to calculate the predetermined time period based on the gait signal.

11. The apparatus of claim 9, wherein the processor is configured to produce the second signal at the second time when the gait signal fails to cross the second threshold within the predetermined time period after the first time.

12. The apparatus of claim 9, further comprising:
a wireless transmitter configured to transmit the first signal and the second signal to a stimulation system.

13. The apparatus of claim 9, wherein the processor is configured to detect the plurality of gait events, the plurality of gait events including a heel-on event and a subsequent heel-off event, the processor configured calculate the predetermined time period based on a time between the heel-on event and the heel-off event.

14. The apparatus of claim 9, wherein:
the first gait event is a heel-off event associated with a first time; and
the processor is configured calculate the predetermined time period based on a time between the heel-off event and a heel-on event associated with a second time earlier than the first time.

15. The apparatus of claim 9, wherein:
the first gait event is a heel-off event associated with a first time; and
the time period is greater than a time period between the heel-off event and a heel-on event associated with a second time earlier than the first time.

16. An apparatus, comprising:
a sensor configured to produce a gait signal as a function of time, the gait signal associated movement of a lower limb of a patient, the gait signal including a plurality of maximums and a plurality of minimums; and
a processor configured to calculate a dynamic range of the gait signal based at least in part on the plurality of maximums and the plurality of minimums, the processor configured to calculate, based on the dynamic range of the gait signal, a first threshold and a second threshold, the first threshold associated with a first gait event, the second threshold associated with a second gait event,
the processor configured to produce a first signal when the gait signal crosses the first threshold at a first time, the processor configured to produce a second signal when the gate signal crosses the second threshold within a predetermined time period after the first time, the processor configured to produce a third signal when the gate signal does not cross the second threshold within the predetermined time period after the first time.

17. The apparatus of claim 16, wherein the processor is configured to identify as invalid at least one of a maximum from the plurality of maximums or a minimum from the plurality of minimums.

18. The apparatus of claim 16, wherein the processor is configured to calculate the predetermined time period based on the gait signal.

19. The apparatus of claim 16, further comprising:
a housing configured to contain the sensor and the processor; and
a wireless transmitter disposed within the housing, the wireless transmitter configured to transmit the first signal and the second signal to a stimulation system.

* * * * *